(12) United States Patent
Berlatzky et al.

(10) Patent No.: US 8,614,790 B2
(45) Date of Patent: Dec. 24, 2013

(54) OPTICAL SYSTEM AND METHOD FOR INSPECTION OF PATTERNED SAMPLES

(75) Inventors: Yoav Berlatzky, Kfar Uriva (IL); Ido Kofler, Givataaim (IL); Doron Meshulach, Ramat-Gan (IL); Kobi Barkan, Holon (IL)

(73) Assignee: Applied Materials Israel, Ltd., Rehovot (IL)

( * ) Notice: Subject to any disclaimer, the term of this patent is extended or adjusted under 35 U.S.C. 154(b) by 0 days.

(21) Appl. No.: 13/323,591

(22) Filed: Dec. 12, 2011

(65) Prior Publication Data
US 2013/0148114 A1   Jun. 13, 2013

(51) Int. Cl.
*G01J 3/02*   (2006.01)

(52) U.S. Cl.
USPC ........................................ 356/310; 356/237.6

(58) Field of Classification Search
USPC ............................. 356/310, 330, 237.2–237.6
See application file for complete search history.

(56) References Cited

U.S. PATENT DOCUMENTS

| | | | |
|---|---|---|---|
| 6,686,602 B2 | 2/2004 | Some | |
| 7,130,039 B2 | 10/2006 | Vaez-Iravani et al. | |
| 7,295,303 B1* | 11/2007 | Vaez-Iravani et al. | 356/237.4 |
| 2002/0088952 A1 | 7/2002 | Rao et al. | |
| 2009/0323052 A1* | 12/2009 | Silberstein et al. | 356/237.5 |
| 2012/0092656 A1 | 4/2012 | Nakao et al. | |

OTHER PUBLICATIONS

Non-Final Office Action of Dec. 21, 2012 for U.S. Appl. No. 13/323,671, 9 pages.
Final Office Action of Jul. 24, 2013 for U.S. Appl. No. 13/323,671, 12 pages.

* cited by examiner

*Primary Examiner* — Gregory J Toatley
*Assistant Examiner* — Rebecca C Bryant
(74) *Attorney, Agent, or Firm* — Kilpatrick Townsend & Stockton LLP

(57) ABSTRACT

An optical inspection system for inspecting a patterned sample located in an inspection plane includes an illumination unit defining an illumination path, and a light collection unit defining a collection path, each path having a certain angular orientation with respect to the inspection plane. The illumination unit comprises an illumination mask located in a first spectral plane with respect to the inspection plane and the light collection unit comprises a collection mask located in a second spectral plane with respect to the inspection plane being conjugate to the first spectral plane. Arrangements of features of the first and second patterns are selected in accordance with a diffraction response from said patterned sample along a collection channel defined by the angular orientation of the illumination and collection paths.

9 Claims, 11 Drawing Sheets
(11 of 11 Drawing Sheet(s) Filed in Color)

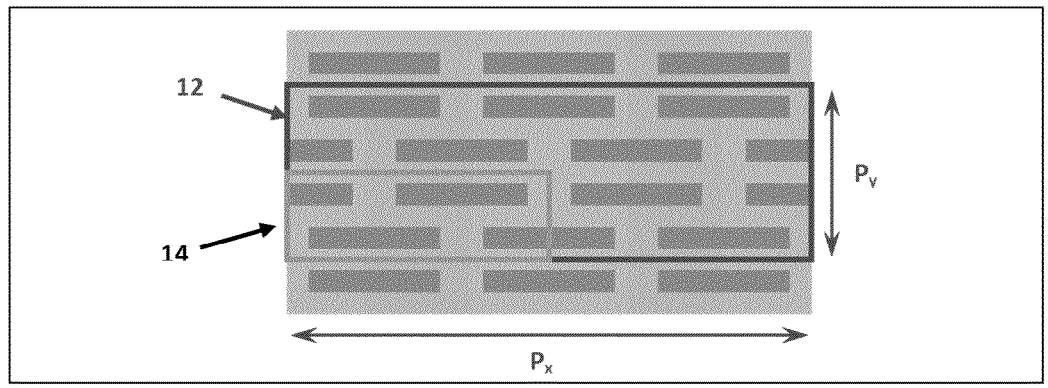
Fig. 6A
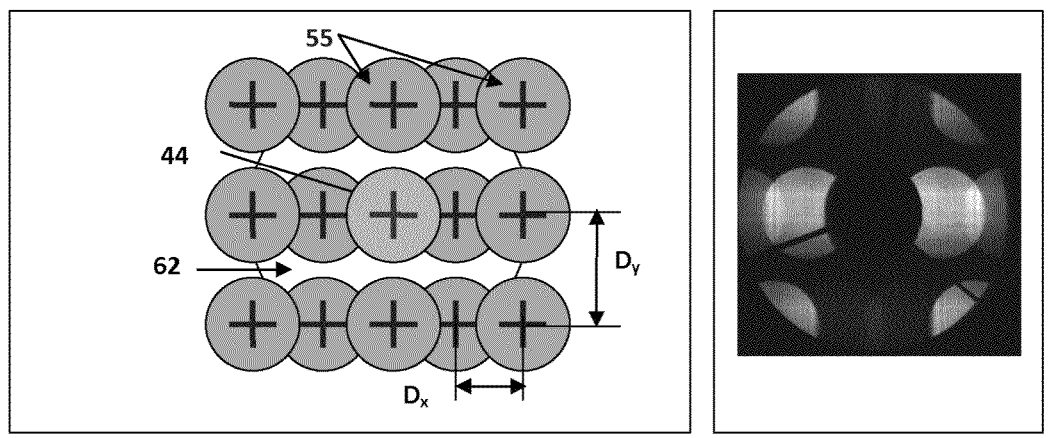
Fig. 6B                    Fig. 6C

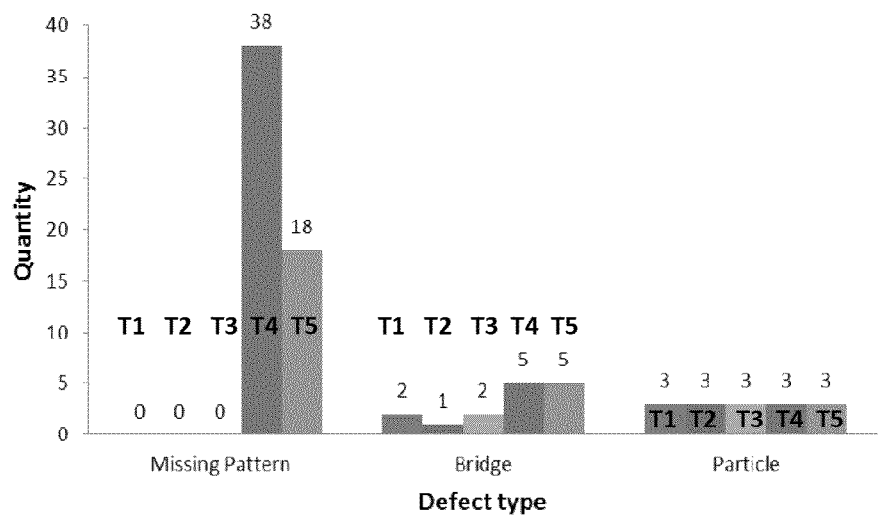
Fig. 12
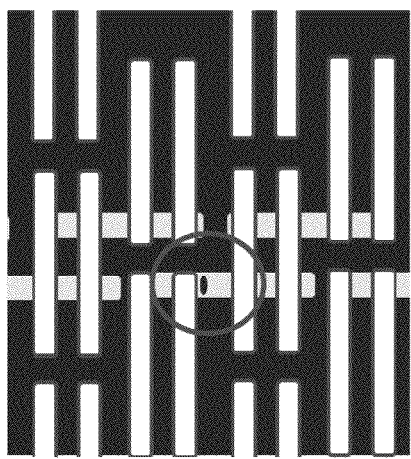 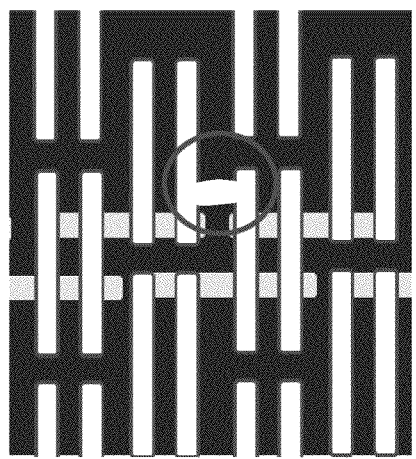
Fig. 13A                    Fig. 13B

OPTICAL SYSTEM AND METHOD FOR INSPECTION OF PATTERNED SAMPLES

FIELD OF THE INVENTION

This invention is in the field of optical inspection and relates to a system and method for inspecting patterned samples.

BACKGROUND

A decrease in size of the features of a pattern in a semiconductor wafer challenges resolution limits of optical inspection systems. A typical size for features of a pattern corresponding to electronic units is defined by design rules (DRs) of semiconductor wafers.

The shrinking design rules of semiconductor wafers lead to new challenges in optical inspection of the wafer. Pattern inspection techniques typically utilize a so-called bright field (BF) inspection mode.

Traditional BF inspection systems, which are based on resolved imaging of the pattern on a wafer, are limited in their spatial resolution due to diffraction limits of the optics in the imaging system. Using shorter wavelengths, such as the deep ultraviolet (DUV) spectral range, and increasing the numerical aperture (NA) of the imaging system may generally improve bright field imaging by reducing the diffraction limited spot size. However, when the typical dimension of the pattern feature becomes less than 90 nm, most of the features on the wafer (especially in array areas) cannot practically be resolved by suitable bright field imaging techniques.

On the other hand, the shrinking DRs result in noticeable diffractive effects from the pattern on the wafer. The diffraction orders are highly spread and the main diffraction lobes have high angular separation from the specular reflection of the pattern, i.e., zero order of diffraction. Such spatial separation of diffraction orders may be utilized for spatial filtering of the diffraction lobes. This can be utilized for blocking the diffraction lobes corresponding to large pitch components of the pattern and thus inspecting mainly for defects detectable as those causing light scattering in all directions. This technique presents dark field (DF) inspection/imaging and provides detection of defects in the pattern, which appear as bright spots on a dark background. DF inspection can be performed by collecting mainly scattered light, e.g., by blocking the specular reflection of light from the main pattern.

Efficiency of detection in dark field inspection mode is based on increases of the signal to noise ratio. Similarly to bright field inspection techniques, increasing the numerical aperture of the system operating in dark field mode enables more efficient collection of light and thus increases detection efficiency. The signal to noise ratio may also be increased by filtering light components of the diffraction orders providing a darker background and thus simplifying the detection of defects.

Various dark field imaging techniques have been developed aimed at improving the system performances.

For example, U.S. Pat. No. 6,686,602 describes an apparatus for spatial filtering including a Fourier lens, adapted to collect radiation emitted from a point and to separate the collected radiation into spatial components in a Fourier plane of the lens, and a programmable spatial filter, positioned at the Fourier plane. An image sensor is optically coupled to capture an image of the spatial components of the collected radiation in the Fourier plane, while the components are incident on the filter. A filter controller is coupled to receive and analyze the image captured by the image sensor and, responsive thereto, to control the spatial filter so as to block one or more of the spatial components.

U.S. Pat. No. 7,130,039 describes a compact and versatile multi-spot inspection imaging system employing an objective for focusing an array of radiation beams to a surface and a second reflective or refractive objective having a large numerical aperture for collecting scattered radiation from the array of illuminated spots. The scattered radiation from each illuminated spot is focused to a corresponding optical fiber channel so that information about a scattering may be conveyed to a corresponding detector in a remote detector array for processing. For patterned surface inspection, a cross-shaped filter is rotated along with the surface to reduce the effects of diffraction by Manhattan geometry. A spatial filter in the shape of an annular aperture may also be employed to reduce scattering from patterns such as arrays on the surface. In another embodiment, different portions of the same objective may be used for focusing the illumination beams onto the surface and for collecting the scattered radiation from the illuminated spots simultaneously. In another embodiment, a one-dimensional array of illumination beams is directed at an oblique angle to the surface to illuminate a line of illuminated spots at an angle to the plane of incidence. Radiation scattered from the spots are collected along directions perpendicular to the line of spots or in a double dark field configuration.

SUMMARY OF THE INVENTION

There is a need in the art in facilitating inspection of patterned samples to detect defects in the samples. The defects may be of the type other than those associated with a pattern itself, such as foreign particles (e.g., dust) on the surface of the sample. Also, the defects to be detected may be associated with a pattern having relatively small features (smaller than the diffraction limit of the optics used), i.e., a pattern which has spatial frequencies (pattern periodicity) higher than the optical resolution limit of the inspection system. Moreover, it might be the case that periodicity of the pattern is different along x- and y-axes.

In the traditional bright field (BF) inspection systems, the defect detection sensitivity depends on the optical resolution of the system and the pattern contrast, which in turn is correlated with a relation between the illumination wavelength 2 and the numerical aperture NA of the optics. When dealing with patterns having the pitch size (features) much smaller than the optical spot size on the wafer (diffraction limited spot or optical resolution), BF inspection reaches its limit and certain defects cannot be detected by traditional BF inspection systems.

Scattered light detection, or dark field (DF) mode, involves collection of scattered light outside the solid angle of illumination or specular reflection, and enables one to overcome the resolution barriers, since the detection is determined by the signal-to-noise ratio (SNR) and not by pattern contrast, which is impacted by the optics resolution. Unresolved dark scenarios are typical of repetitive dense arrays, where distinct diffraction lobes at specific locations are formed. In order to enable DF detection mode, such diffraction lobes are to be blocked by spatial filtering (spatial mask).

It is often the case that inspection of patterned samples needs to be carried out with both bright-field and dark-field modes, requiring selective switching between these modes of inspection.

The present invention provides a novel optical inspection technique enabling optimal performance of a dark field inspection mode irrespective of the actual location of a light collection channel with respect to an illumination/specular reflection azimuth and elevation. To this end, the invention utilizes an appropriate arrangement of illumination and collection masks (masks' accommodation and patterns) to optimize light collection with desirably high resolution, i.e., enabling a sufficiently large collection region (for a given light collection channel) with a desirably small illumination spot. It should be noted that the mask (illumination and/or collection pattern) may have a static pattern or may be constituted by an electronic spatial coding in which case the pattern may be dynamic. In any case, the technique of the present invention provides for appropriately varying the mask pattern, e.g., by using a switching mechanism for replacing one mask by another having a different static pattern or for appropriately varying a code of the electronic unit (spatial light modulator).

It should be understood that a bright-field inspection mode is aimed at inspecting the pattern itself. In a bright-field mode, an imaging system collects light reflected from the sample including light components associated with diffraction orders (resulting from the periodicity of the pattern) providing information indicative of as many spatial details of the inspected pattern as possible by optical limitations of the system. On the other hand, a dark-field inspection mode utilizes collection of scattered light while blocking or significantly reducing collection of light reflected directly from the pattern on the sample.

As indicated above, dark-field inspection mode includes collection of light scattered from a possible defect. The defect is identified as a bright spot over dark background. The collection of scattered light can be done by orienting a light collection channel outside the azimuth and elevation of propagation of specular reflection from a sample, thus collecting substantially scattered light (signal) and also high order diffraction components (noise) having relatively low intensity. In other configurations, dark-field imaging techniques may utilize light collection with angular orientation of a collection channel passing through or in the vicinity of the orientation of specular reflection path. A collection mask can be utilized for blocking light components associated with diffraction orders and thus increase signal to noise ratio (SNR) and improving efficiency of the defect detection.

The present invention is based on the understanding that angular location of diffraction orders resulting from periodicity of the pattern is defined by a relation between an illumination channel and the pattern on the sample under inspection. Blockage of the diffraction orders actually results in a dark-field inspection mode.

According to the invention, the dark-field inspection is optimized (in the meaning of signal-to-noise improvement) while with a desirably small illumination spot, by utilizing an appropriately designed illumination mask. The illumination mask may be formed by one or more apertures of a non-circular, elongated geometry, e.g., oval-like or polygonal-like aperture(s), or generally an aperture having different lengths along its longitudinal and transverse axes. Alternatively or additionally, the illumination mask may be formed by an array (generally at least two) of apertures (of circular or not geometry). In any case, the aperture(s) of the illumination mask is/are arranged in accordance with an arrangement of the light blocking regions of the collection mask. The aperture may be configured to provide a so-called "soft illumination", i.e., a certain transmission gradient across the aperture.

In the simplest case of "normal inspection mode", where illumination and collection channels coincide, the apertures of the illumination mask are made in or aligned with at least some of the blocking regions of the light collection mask. In a generalized case, where illumination and collection channels may or may not coincide (oblique illumination), the illumination and collections masks are located at corresponding spectral planes with respect to the sample plane. It should be understood that these corresponding planes are typically Fourier planes with respect to the sample, or can be referred to as conjugate planes of one another (i.e., "pupil" and "image" planes and vice versa). In this case, an arrangement of apertures of the illumination mask and an arrangement of the blocking regions of the collection mask are selected to optimize (maximize) an effective collection region. Light passing through the illumination mask and returned from the pattern of the sample forms diffraction lobes each being an image of the illumination mask. Thus, by varying the shape of the diffraction lobes (i.e., by appropriately designing the illumination mask) the collection region of scattered light can be increased.

It should be understood that the technique of the present invention is especially useful for inspection of patterned samples having a certain asymmetry along two axes of the sample (different periodicities of the pattern along different axes). As will be explained below, a typical pitch size of the pattern along a certain axis (defined as an x- or y-axis along the surface of the sample) determines a distance between the centers of diffraction lobes along the same axis. When the typical pitch size of the pattern is different along the x- and y-axes, the arrangement of the diffraction lobes is different. Assuming a patterned sample having a substantially rectangular optical unit cell (reappearing pattern which spans the surface), having larger pitch size along the x-axis, the distances between the centers of the diffraction lobes along the x-axis will be smaller than those along the y-axis. The technique of the present invention may utilize the asymmetry of the pattern to optimize the collection region by appropriately shaping the illumination pupil, and thus the diffraction lobes, to stretch the diffraction lobes along one axis, while keeping them narrow along the other axis. More specifically, if the pattern has larger pitch size along the x-axis, the illumination pupil will be relatively wider along the x-axis and relatively narrow along the y-axis. Moreover, the use of multiple illumination apertures arranged with the same relation between their centers as that of the diffraction lobes pattern increases the amount of illumination reaching the patterned surface and thus increases the efficiency of the inspection. Utilizing an array of apertures may also provide for a smaller illumination spot on the sample. A smaller illumination spot increases accuracy and sensitivity of the inspection.

Thus, according to one broad aspect of the invention, there is provided an optical inspection system defining an inspection plane for inspecting a patterned sample located in said inspection plane. The system comprises an illumination unit defining an illumination path of a certain angular orientation with respect to the inspection plane, and a light collection unit defining a collection path of a certain angular orientation with respect to the inspection plane. The illumination unit comprises an illumination mask located in a first spectral plane with respect to the inspection plane and comprising a first predetermined discontinuous pattern of an array of light transmitting regions. The light collection unit comprises a collection mask located in a second spectral plane with respect to the inspection plane being conjugate to the first spectral plane, the collection mask comprising a second predetermined pattern of spaced-apart light blocking regions. The arrangements of features of the first and second patterns are selected in accordance with a diffraction response from the patterned sample along a collection channel defined by the angular orientation of the illumination and collection paths, such that the light transmitting regions of the first pattern are in a predetermined alignment with the blocking regions of the second pattern.

It should be understood that light passage through the illumination mask actually creates structured light of the first spatial pattern, while light passage through the collection mask creates structured light of the second spatial pattern.

The first and second spectral planes are Fourier planes with respect to the inspection plane. Such first and second spectral planes may be substantially coinciding planes (normal incidence mode), or may have different angular orientation with respect to the inspection plane (oblique incidence mode). The light collection channel may be oriented along propagation of light specularly reflected from a spot illuminated by the illumination channel (bright-field orientation), or outside the specular reflection propagation path (dark-field orientation).

Preferably, the first pattern in the illumination mask comprises the array of transmitting regions arranged with a spaced-apart relationship, where each transmitting region has a substantially circular geometry. The light transmitting region may be configured as an aperture having a transmission gradient across the aperture.

According to some embodiments, at least one of the illumination and collection masks comprises an electronic coding unit; and in some other embodiments at least one of the illumination and collection masks comprises a patterned structure as a physical element. In any case, the system may comprise a switching unit for replacing at least one of the illumination and collection patterns, either by replacing the masks or by varying a pattern of an electronic coding unit.

According to another broad aspect of the invention, there is provided an optical inspection system defining an inspection plane for inspecting a patterned sample located in the inspection plane, the system comprising: an illumination unit defining an illumination path of a certain angular orientation with respect to the inspection plane, and a light collection unit defining a collection path of a certain angular orientation with respect to the inspection plane, wherein the illumination unit comprises an illumination mask located in a first spectral plane with respect to a sample plane, the illumination mask comprising a first pattern defining an array of spaced-apart light transmitting regions, each having a substantially circular geometry;

the light collection unit comprises a collection mask located in a second spectral plane with respect to the sample plane being conjugate to the first spectral plane, the collection mask comprising a second predetermined pattern of spaced-apart light blocking regions;

arrangements of features of the first and second patterns is selected in accordance with a diffraction response from said patterned sample along a collection channel defined by the angular orientations of the illumination and collection paths, such that said array of spaced-apart substantially circular light transmitting regions of the first pattern is in alignment with the blocking regions of the second pattern.

According to yet another broad aspect of the invention, there is provided an optical inspection system defining an inspection plane for inspecting a patterned sample located in the inspection plane, the system comprising: an illumination unit defining an illumination path of a certain angular orientation with respect to the inspection plane, and a light collection unit defining a collection path of a certain angular orientation with respect to the inspection plane. Each of the illumination and collection units comprises a spatial mask located in a spectral plane with respect to a sample plane. One of the masks comprises a first pattern defining a first array of spaced-apart light transmitting regions spaced by light blocking regions, and the other mask comprises a second predetermined pattern defining a second array of spaced-apart light transmitting regions spaced by light blocking regions. The arrangements of regions of the first and second patterns are selected in accordance with a diffraction response from said patterned sample along the collection path, such that the light transmitting regions of the first pattern are in a predetermined alignment with the blocking regions of the second pattern.

According to yet further broad aspect of the invention, there is provided a method for use in optical inspection of patterned samples. The method comprises: illuminating the sample with light propagating along an illumination channel having a predetermined numerical aperture and a predetermined angular orientation with respect to the inspection plane, thereby creating an illuminating spot on the sample and causing a diffraction response from the sample; and collecting light returned from the sample along a collection channel of a predetermined angular orientation with respect to the inspection plane. The illumination comprises creating first structured light of a first spatial pattern in a first spectral plane with respect to the inspection plane, and the light collection comprises creating second structured light of a second spatial pattern in a second spectral plane with respect to the inspection plane. The features of the first and second spatial patterns are selected in accordance with the diffraction response propagating along the collection channel, such that light components of the first structured light are in a predetermined alignment with spaces between light components of the second structured light, thereby providing a desired relation between a collection region defined by the light components of the second structured light and a dimension of the illumination spot.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to understand the invention and to see how it may be carried out in practice, embodiments will now be described, by way of non-limiting example only, with reference to the accompanying drawings, in which:

FIGS. 6A to 6C illustrate an example of a periodic structure (pattern) along the surface of a sample (FIG. 6A) and a diffraction pattern generated by light returned from the surface (FIGS. 6B and 6C);

FIG. 12 illustrates detection rates of different defect types utilizing dark-field mode, bright-field mode, and the technique of the present invention; and FIGS. 13A and 13B exemplify two types of defects which can be identified using the technique of the present invention, where FIG. 13A exemplifies a "missing pattern" type defect and FIG. 13B exemplifies a "bridge" type defect.

DETAILED DESCRIPTION

The general principles of bright field and dark filed inspections of patterned samples are illustrated in FIGS. 1A to 1D and FIGS. 2A to 2D. To facilitate understanding, the same reference numbers are used for identifying components that are common in all the examples.

It should be noted that, generally, a pattern on the sample's surface may be in a form of a surface relief as shown in FIGS. 1A to 1D, and/or may be defined by regions of different optical properties with respect to given illumination, i.e., regions of different reflection, absorption or transmission properties.

Figure 1A:
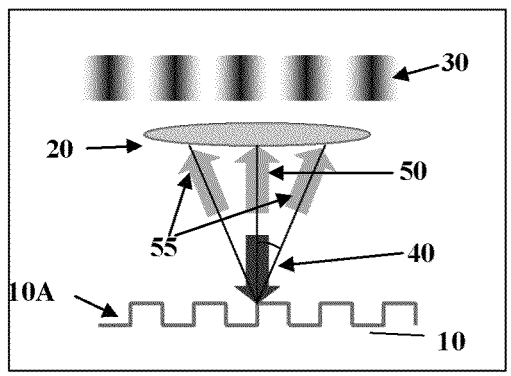
FIGS. 1A-1D illustrate the general principles of bright field inspection of patterned samples.

In FIG. 1A, a sample 10 having a periodic pattern of a certain spatial frequency on its surface 10A is illuminated by an optical beam 40 of a certain wavelength λ (e.g., including ultraviolet and/or infra red illumination) creating an illumination spot on the surface of the sample 10. Light is reflected back from the pattern 10A in different directions according to several diffraction orders. The zero-order diffraction component 50 is that of specular reflection angle, while other diffraction orders 55 are reflected in different angular directions determined inter alia by the wavelength λ and the periodicity of the pattern 10A. These light components (50 and 55) returned from the sample are collected by a lens unit 20 (including one or more lenses) having a certain numerical aperture (NA) and forming an image 30 of the patterned surface on an image plane (detector plane).

Figure 1B:
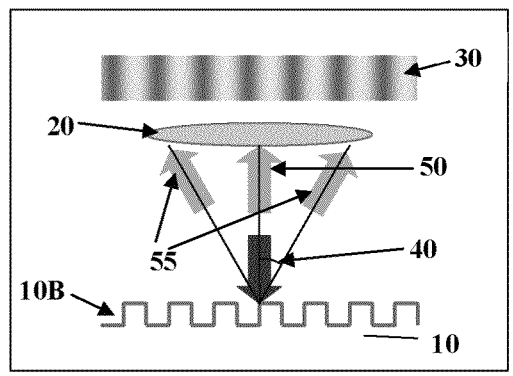
Figure 1C:
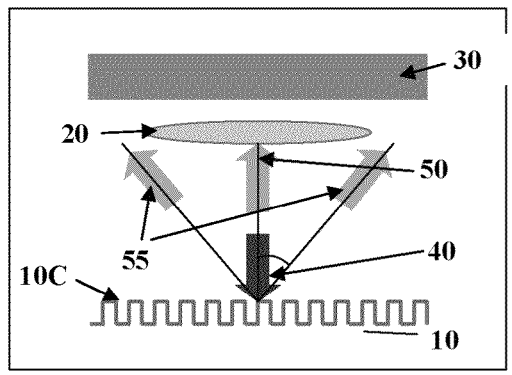

A pattern of smaller design rule (DR), i.e. having higher spatial frequency and smaller patterned features, responds to the given illumination (i.e., spot size and wavelength) with higher spreading of the diffraction lobes (diffraction orders) into larger angles around the zero order diffraction. Indeed, in FIG. 1B the DR dimension (or the periodicity) of the pattern 10B is smaller than that of pattern 10A but is still within the resolution limits of the light collection lens unit 20, and at least the light components 55 of the first diffraction orders are collected by the numerical aperture of the lens unit 20. As can be seen in FIG. 1B, a resulting image 30, although having lower contrast as compared to that of FIG. 1A, allows detection (visualization) of the pattern. However, as shown in FIG. 1C, when a pattern 10C has small features, going beyond the resolving limit of the collection lens unit 20, even the light components 55 of the first diffraction orders might not be collected by the lens unit 20 and thus no pattern can be resolved in the image plane 30.

Figure 1D:
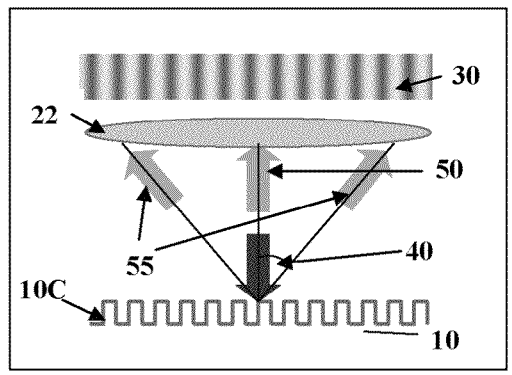

In order to enable imaging of the surface pattern with smaller DR (or higher frequency), the numerical aperture of the collection lens unit 20 can be enlarged. This is shown in FIG. 1D. The use of higher numerical aperture of collection allows collection of light components from higher diffraction orders and provides a better resolved, higher-contrast image 30 of the patterned surface.

In case of semiconductor wafer inspection or the like, where the features of a pattern become smaller, there is a practical limit for the numerical aperture which can be used for imaging the pattern. Hence, dark field inspection techniques may be used for detecting defects in such small-feature patterned surfaces by collecting light scattered from the surface.

As indicated above, dark field imaging may be based on collection of scattered light propagating along path(s) far from the zero order of diffraction, thus reducing the effects (noise) of light components associated with diffraction orders from the pattern in the collected light. Alternatively or additionally, dark field imaging may be based on blockage of the diffraction lobes returned from the sample being either specular reflection or diffraction orders (zero order and higher orders), while collecting returned light propagating with angles around those of diffraction lobes (i.e., scattered light).

Figure 2A:
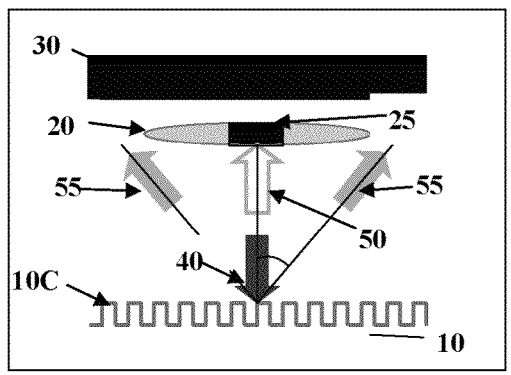
FIGS. 2A-2D illustrate the general principles of dark field inspection for defect detection in patterned samples.
Figure 2B:
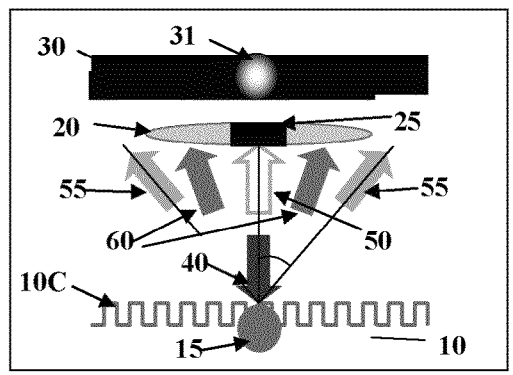
Figure 2C:
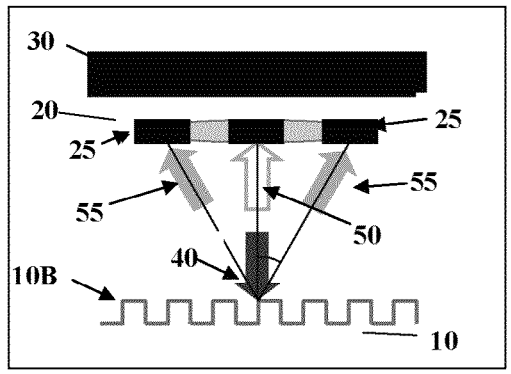
Figure 2D:
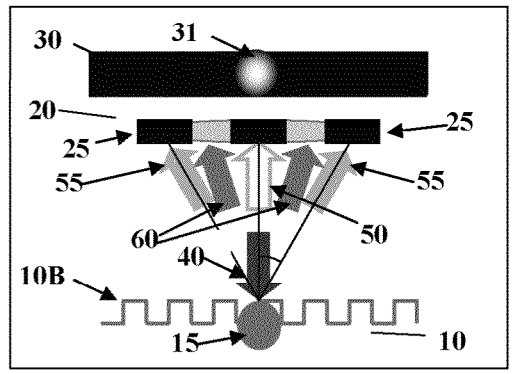

FIGS. 2A to 2D exemplify the principles of dark field inspection of patterned samples, such as semiconductor wafers. FIGS. 2A and 2C illustrate a case with no defect in the patterned region of the sample, and FIGS. 2B and 2D illustrate a case where a defect (e.g., dust particle) on the sample is detected.

In FIG. 2A, a light beam 40 illuminates a pattern 10C on the sample's surface, and light returned from the illuminated spot includes specular reflection component (zero order of diffraction) 50 and higher diffraction orders 55 associated with the periodicity of the pattern 10C. At least a part of the returned light is collected by a collection system, including a lens unit 20 and a collection mask 25. The latter is configured to block light components propagating in the direction of the specular reflection 50 and to transmit light components propagating in other directions. If the periodic pattern has no defects, blockage of an appropriate part of the returned light, as shown in FIGS. 2A and 2C, results in a dark image.

FIG. 2B illustrates a patterned sample having a defect 15. The defect scatters light in many directions and not only those of the diffraction orders of the periodic pattern. Hence, the returned light includes light component(s) 60 propagating towards the collection system at angle(s) other than those of the diffraction orders' components 50 and 55. These scattered light components 60 are collected by the lens unit 20 and are allowed (by mask 25) to pass to the image plane 30 resulting in an image of the defect in the form of a bright spot 31 on the dark background.

FIGS. 2C and 2D illustrate the light propagation schemes for a sample having lower spatial frequency of the pattern (larger DR) without and with (respectively) a defect in the patterned area. These figures show an example where some higher diffraction orders are collected by a collection unit, due to large numerical aperture of a collection lens unit and/or due to lower spatial frequency of the pattern. In this case, a collection unit includes a collection mask 25 configured to block these higher diffraction orders, as well as the zero order.

The inventors have found that sensitivity of defect detection can be increased by maximizing a combined effective area/region of light collection and illumination. The effective collection region is defined by the dimension of transmitting regions (apertures) of the collection mask, while the effective illumination region is defined by the dimension of the illumination aperture/pupil of the system. However, since the use of a larger illumination pupil results in larger diffraction lobes, which are to be blocked, the effective collection region would be reduced in size, or be entirely eliminated if the lobes completely overlap. The inventors have found that by appropriately selecting the size and shape of the illumination pupil, the shape of the diffraction lobes can be affected so as to provide a desirably large effective collection region, thus increasing the sensitivity of defect detection. A proper design of the illumination pupil, together and in accordance with a design of the collection mask (for blocking the diffraction lobes returned from the pattern), allows for both increasing the signal to noise ratio (SNR) and improving the resolution, thus enabling effective detection of smaller defects.

Figure 3A:
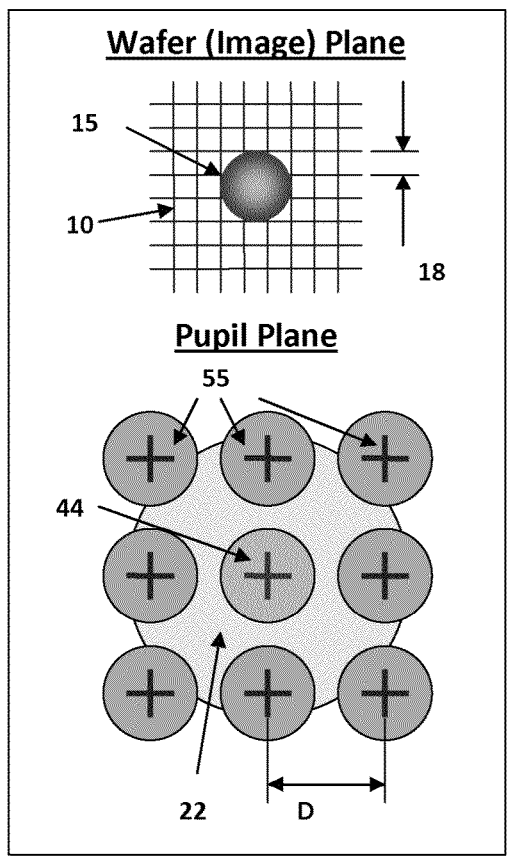
FIGS. 3A and 3B schematically illustrate a relation between the size of an illumination spot and diffraction lobes, affecting the collection region dimension.
Figure 3B:
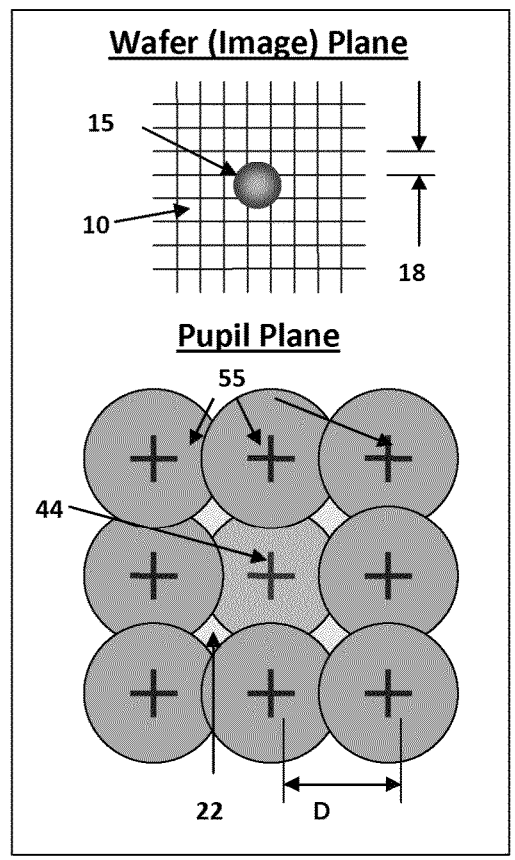

The shape of the illumination pupil (formed by one or more illumination apertures) affects the shape and size of the diffraction lobes associated with light returned from the pattern on the surface of the sample. Reference is made to FIGS. 3A and 3B schematically illustrating the relation between the illumination spot size and the diffraction lobes parameters.

A wafer (sample) 10 surface/plane is shown having a pattern with a certain pitch size 18, and an illumination spot 15 within the pattern. Also shown in the figures is a pupil plane with a potential collection region 22 (i.e. a region in the pupil plane from which light can be collected with a given numerical aperture) projected thereon, and an illumination pupil 44. As shown, few diffraction lobes 55 propagate along paths intersecting with the collection region 22. The effective collection area/region 22 is thus limited by these diffraction lobes 55 which are to be blocked for reducing noise in darkfield inspection. The illuminating spot 15 and the illuminating pupil 44 are typically a Fourier transform pair; similarly, the illumination spot 15 and the diffraction lobes 55 are Fourier transform pairs. Thus, a larger spot size 15 (as shown in FIG. 3A) results with smaller diffraction lobes 55, while a smaller spot size (as shown FIG. 3B) results with larger diffraction lobes. Moreover, the diffraction lobes 55 are substantially an image of the illuminating pupil 44.

Typical dark field imaging systems utilize a collection mask configured for blocking the diffraction lobes in order to allow detection of scattered light only. Using a partially blocking collection mask creates a design tradeoff between the effective collection area and the size of the illumination spot on the sample's surface affecting the size of the diffraction lobes to be blocked. It should be noted that the spacing between centers of the diffraction lobes is determined by the periodicity of the pattern on the surface of the sample (wafer), e.g., at the Fourier plane the spacing between the diffraction lobes is given by:

$$D = \lambda/P \qquad \text{eqn. 1}$$

where D is the spacing between the centers of the diffraction lobes 55, P is the pitch size 18 of the pattern on the sample and $\lambda$ is the wavelength used in the system.

Decreasing the illumination spot area 15 increases the detection sensitivity since the available illumination intensity (typically laser power) is concentrated onto a smaller area thus increasing the intensity of the response. Moreover, a smaller illumination spot size 15 may reduce false alarms caused by roughness of the wafer surface 10 and allow better localization of detected defects. On the other hand, a smaller illumination spot 15 generated by a larger illumination pupil 44 (FIG. 3B) also results in larger diffraction lobes 55 returned from the surface of the wafer 10. Large diffraction lobes reduce the effective collection area/region which can be used for dark field imaging. As can be seen from FIG. 3B, utilizing a collection mask configured to block diffraction lobes 55 leaves only a very limited area that can practically be used for collection of scattered light, which area would be entirely eliminated if the lobes completely overlap.

The present invention is aimed at optimizing detection by providing an optimized balance between the size of the imaging pupil and the effective collection region, while providing effective spatial filtering of light being collected (i.e., blockage of the diffraction lobes).

Figure 4:
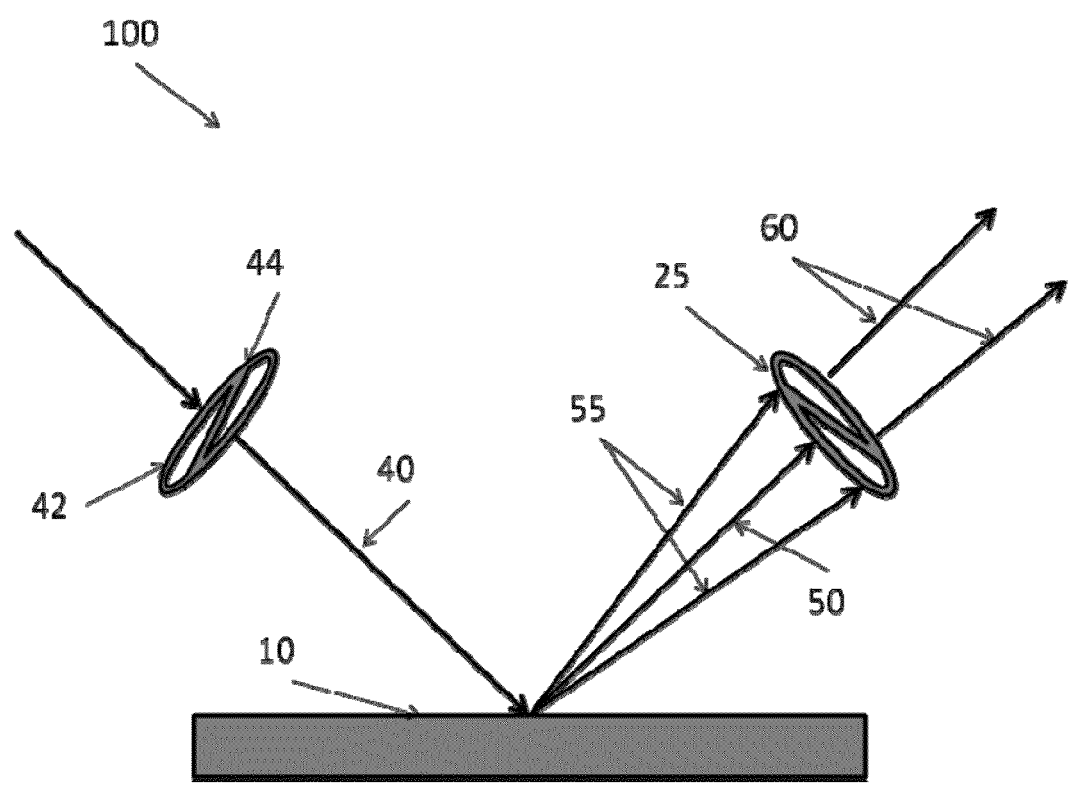
FIG. 4 schematically exemplifies a light propagation scheme in a system of the present invention for pattern inspection of a patterned sample.

Reference is made to FIG. 4 schematically illustrating an example of the light propagation scheme in a system 100 of the invention for inspection of a patterned sample 10. The system 100 utilizes an illumination channel (associated with an illumination unit, which is not specifically shown) including an illumination mask 42 configured to provide beam shaping to an illuminating light beam 40 propagating towards the sample 10 to be inspected. The illumination channel also typically includes various optical components including at least focusing optics which are not specifically shown. The illumination mask 42 has a predetermined pattern 44 of spaced apart light blocking and transmitting regions, the transmitting regions (apertures) defining an illumination pupil 44 of the system. An illuminating spot on the surface of the sample 10 is thus formed by multiple light components. Light returned from the patterned surface typically includes a diffraction pattern, i.e., light components propagate in a discrete set of diffraction lobes including that of specular reflection 50 (zero order of diffraction) and a plurality of diffraction orders 55 around the zero order diffraction lobe. If the periodicity of the pattern of the sample is broken/damaged due to a defect located in the illumination spot, at least some light is scattered from the defect in random directions providing randomly scattered light 60. Light returned from the illumination spot (including scattered light) propagates along a collection channel towards a collection unit including a collection mask 25.

It should be noted, although not specifically shown, that the collection unit typically includes at least imaging optics which are not shown here. The collection mask 25 is configured to partially transmit light incident thereon. For dark field inspection, the collection mask is configured for blocking light components associated with the diffraction lobes and transmitting only scattered light. This is aimed at detection of defects in the sample.

Generally, the system 100 may include a switching unit, configured for switching any one of the collection mask 42, the illumination mask 25 or any other optical element specially designed for inspection of a predetermined pattern (e.g., a donut mirror, as will be described below) to thereby enable inspection of different samples (different patterns), as well as enable variation of inspection techniques. The switching unit may be preloaded with a predetermined set of optical elements or generally spatial coders designed according to a set of samples to be inspected, and configured to switch between different coders in response to a predetermined command from an operator/computer. It should thus be noted that the switching unit may be configured to mechanically switch between physical elements, or vary the spatial code design. For example, an SLM unit (e.g., an LC panel) may be used as an optical mask (illumination mask or collection mask) and the pattern thereof may vary in accordance with a proper commend.

Both the illumination mask 42 and the collection mask 25 are located in mutually conjugate planes, which are preferably Fourier planes with respect to the sample plane. The arrangement of blocking and transmitting regions on the collection mask 25 is predetermined according to the pattern of the inspected sample and the illumination pupil 44. The arrangements of the blocking and transmitting regions of the illumination 42 and collection 25 masks are selected together to optimize (maximize) an effective collection region for collection of scattered light components while maintaining a desirably large illumination pupil (desirably small illumination spot).

It should be understood that a mask (illumination mask 42 and/or collection mask 25) is configured as a discontinuous pattern, meaning that at least one of light transmitting regions has a certain discontinuity, e.g., several discrete regions. For example, a mask may include a blocking region surrounded by a transmitting region, in which case the transmitting region has closed loop geometry with a central discontinuity.

Figure 5:
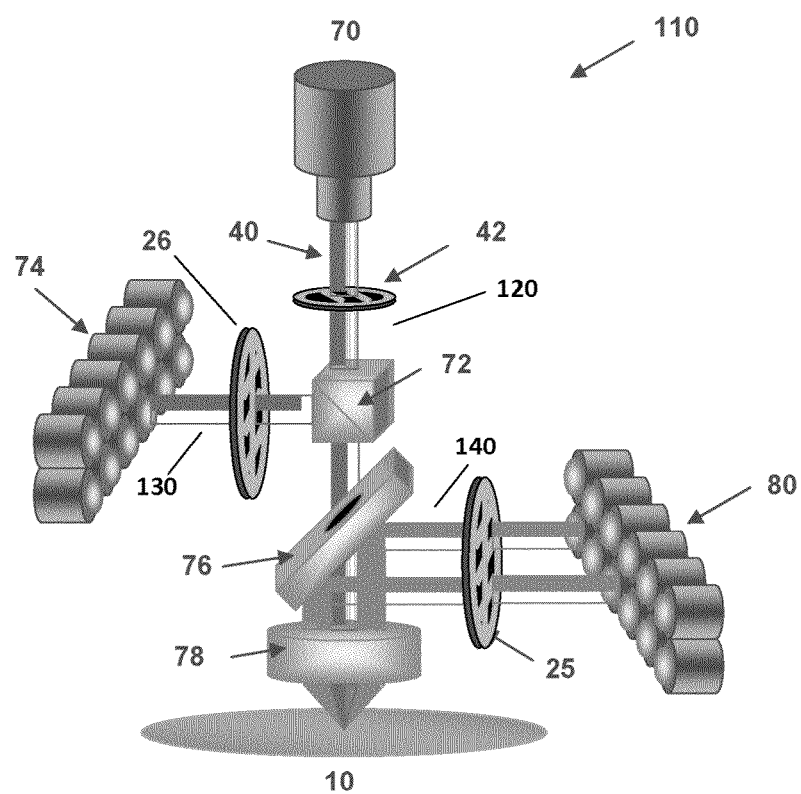
FIG. 5 schematically illustrates another example of a light propagation scheme in an inspection system for inspection of a patterned sample.

One other example of a system 110 for dark field inspection of a sample 10 is shown is FIG. 5. The system 110 includes an illumination channel 120 and two, partially overlapping, collection channels 130 and 140 for bright and dark field imaging, respectively, utilizing separate detection units 74 and 80. The system 110 utilizes a light source unit including high power, deep ultra violet (DUV) laser 70. The illumination and collection channels utilize common focusing/imaging optics, including an objective lens 78, defining an overlapping part of these channels. The dark field imaging channel is separated from the common path by a donut mirror (beam splitter) 76. The illumination channel includes an illumination mask 42, and at least the dark field collection channel includes a collection mask 25. In some configurations of the system 110, Channel 130 also utilize a collection mask 26 for providing dark field imaging as well. It should be noted that such system may be configured with only one of the collection channels 130 and 140.

An input light beam 40 is produced by the light source 70 and directed onto the sample through the illumination mask 42 which provides appropriate beam shaping to the light as described above. The shaped beam passes through the donut mirror 76 and is focused by the objective lens 78 onto the surface of the sample 10 with a desirably small size of the illumination spot. The illumination mask 42 is preferably located at the back Fourier plane with respect to the sample (object plane) in order to allow focusing of light onto the sample with a desirably small light spot. Light returned from the sample is collected by the objective lens 78, and a part thereof impinges onto the central region of the donut mirror 76 being thus transmitted towards the bright field collection channel 130, while the other part of the collected light impinges onto the periphery of the donut mirror 76 and is reflected to the dark field channel 140. In the dark field channel, the collection mask 25 is located and operates to filter out diffraction lobes while allowing passage of the light scattered in directions other than those of the diffraction lobes. The illumination mask 42 and the collection mask 25 are designed as described above. When collection channel 130 is configured to provide dark field imaging, collection mask 26, which may also be designed as described above, is utilized.

It should be understood that the imaging channel 130 can operate as bright-field or as dark-field imaging channel. This can be done using collection mask 26 configured according to the considerations described above for blocking specular reflection and diffraction orders. The illumination mask 42 (illumination pupil), as well as collection mask 26, may be removable and/or replaceable for providing adjustable dark- and/or bright-field inspection of different patterned samples.

In addition, according to some embodiments, it is beneficial to change the shape of donut mirror 76 so that the transitive and reflective regions of the mirror 76 operate as both the illumination pupil (illumination mask 42) and the collection mask 25. This configuration may be used even if the mask design includes several transmitting and blocking regions. For this configuration, the donut mirror 72 should be located at a pupil plane of the system, similarly to spatial filter masks 25, 26 and 42. The transmitting region(s) (hole(s)) of the donut mirror 72 may correspond to the light transmitting regions of illumination mask 42, while the reflecting regions may correspond to the light transmitting regions of collection mask 25 or 26 (alternatively, the transmitting regions of the mirror may correspond to the transmitting regions of the collection mask and the reflecting regions to the transmitting regions of the illumination mask). In some embodiments, a set of several donut mirror elements, each designed for optimal inspection of a different pattern may be mounted on the replacing/switching unit for fast replacing of the mirrors in accordance with the sample to be inspected.

As indicated above, according to the present invention, the appropriate design of the illumination mask and the collection mask is aimed at optimization of the effective collection area; a first mask's pattern (e.g., illumination) is determined in accordance with the pattern on the sample to be inspected, while the second mask's pattern (collection) is determined in accordance with the first mask and vice versa. A relation between the patterns of the illumination and the collection masks will now be described.

FIGS. 6A to 6C illustrate an example of a periodic structure (pattern) along the surface of a sample (FIG. 6A) and diffraction lobes generated by light reflected from the surface (FIGS. 6B and 6C). As shown in FIG. 6A the pattern on the wafer has 4 SRAM unit cells 14 which due to their symmetry generate a single optical unit cell 12. FIG. 6B illustrates a pattern of the diffraction lobes 55 as seen at the Fourier plane. The illumination pupil 44 is shown in overlap with the diffraction lobes pattern, in order to enhance the understanding of the configuration. FIG. 6C shows an image of the diffraction lobes collected using a collection mask which is configured to block only the specular reflection response of the sample.

The optical unit cell 12 shown in FIG. 6A is a rectangular unit having vertical pitch $P_y$ and horizontal pitch $P_x$. As shown in this example, the pattern has different periodicity (pitch) along the x- and y-axes. The diffraction lobes pattern, shown in FIG. 6B, created by light returned from such optical unit cell 12 has vertical spacing $D_y$ and horizontal spacing $D_x$ between the centers of the diffraction lobes 55. In the Fourier plane, the spacing between the diffraction lobes 55 follows equation 1 above. Providing a circular illumination pupil 44, as shown in FIG. 6B, there is very limited potential collection area that can be used for dark field imaging.

Figure 7A:
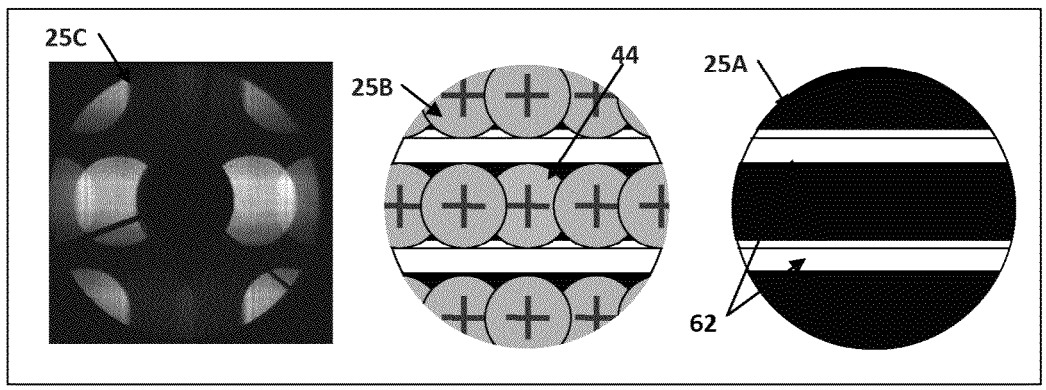
FIGS. 7A to 7C illustrate a relation between an illumination pupil of the imaging system, size and shape of diffraction lobes in the returned light and an effective collection region of the collection channel.
Figure 7B:
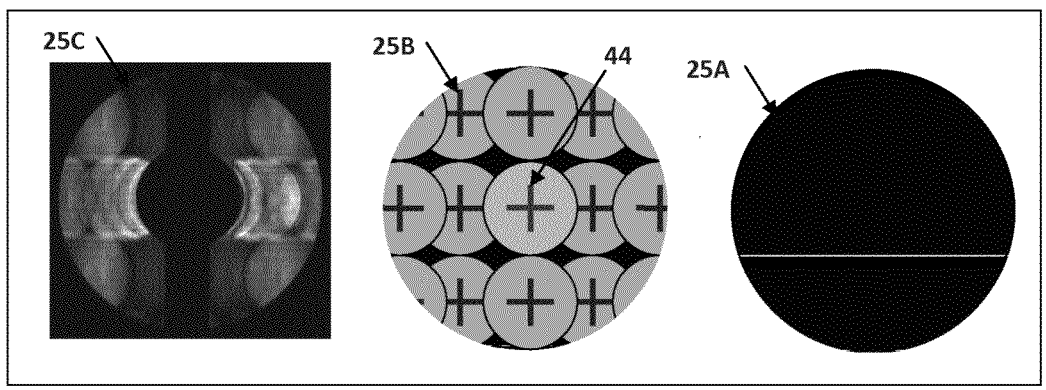
Figure 7C:
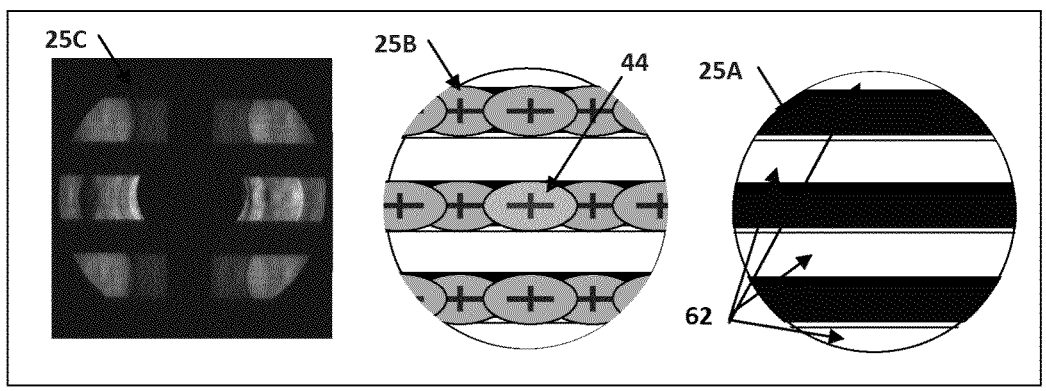

As indicated above, the size and shape of the illumination pupil determine the size of the diffraction lobes, while the periodicity of the inspected pattern determines the spacing between the centers of the diffraction lobes. FIGS. 7A to 7C exemplify a relation between the illumination pupil, the size and shape of the diffraction lobes, and the effective collection area. These figures show different configurations of a collection mask 25A, a position of the diffraction lobes, and illumination pupil 44 (of different sizes and shapes), as projected onto the collection mask 25B, and an image 25C obtainable with this configuration of the illumination and collection channels.

FIG. 7A corresponds to the illumination pupil 44 which is substantially circular and relatively small, thus allowing the collection mask 25A to include moderate effective collection area defined by transmitting regions 62.

FIG. 7B corresponds to the illumination pupil 44 which is larger in order to provide a smaller illumination spot on the surface of the sample. However, with such a configuration, the collection mask in a dark field imaging channel has practically no transmitting regions at all.

FIG. 7C exemplifies the illumination and collection masks' configuration suitable to be used in some embodiments of the invention. In FIG. 7C, the illumination pupil 44 has an oval-like shape constituting an aperture of non-circular or elongated geometry, i.e. with its dimension along one axis being larger than that along the perpendicular axis. In this example, the oval-like illumination pupil 44 has longer major axis extending parallel to the axis of the larger pitch size on the optical unit cell shown in FIG. 6A. The oval-like configuration of the illumination pupil allows for obtaining a smaller illumination spot, while resulting in oval-like shaped diffraction lobes thus opening a space for transmitting regions 62 within the collection mask 25A enabling relatively large collection region.

It should be noted that FIGS. 7A to 7C illustrate the illumination pupil, diffraction lobes and the collection mask on the same plane in order to facilitate the understanding of the relation between them. It should, however, be understood that the illumination pupil and the collection mask are not necessarily overlapping in space, but are typically located in corresponding optical planes (conjugate planes) of the inspection system.

Figure 8A:
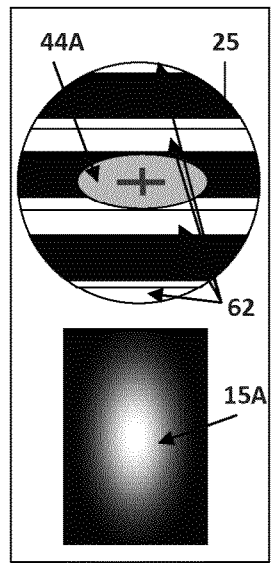
FIGS. 8A to 8C illustrate the general principles underlying the present invention, utilizing an illumination mask having various shapes of light transmitting region (aperture), and configured to optimize the effective collection region with a sufficiently small illumination spot size.
Figure 8B:
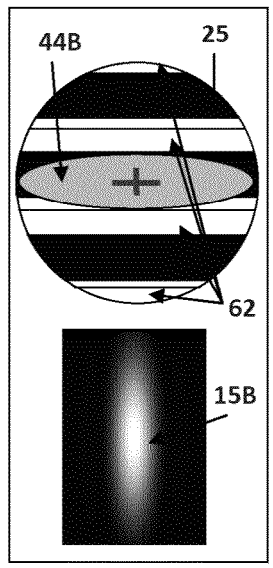
Figure 8C:
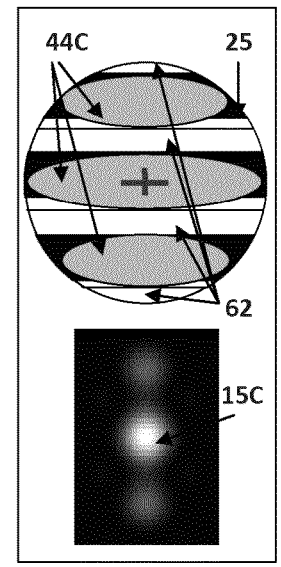

The inventors have found that by modifying the shape of the illumination pupil, or the illumination mask, and accordingly modifying the collection mask the effective collection area can be optimized while maintaining relatively small illumination spot on the sample. FIGS. 8A to 8C illustrate some aspects of the embodiments of the invention utilizing an illumination mask having one or more light transmitting regions (apertures) configured to optimize the effective collection area with decreased illumination spot size.

The examples shown in FIGS. 8A to 8C are configured according to a sample structure as exemplified in FIG. 6A having a rectangular cell unit. These figures show a collection mask 25 designed with three spaced apart blocking regions arranged vertically alternating with four transmitting regions 62 defining together a sufficient collection region while desirably blocking the diffraction lobes. In this particular example, the transmitting and blocking regions are in the form of stripes, however the arrangement and geometry of the blocking and transmitting regions are determined according to the diffraction pattern created by the spatial pattern of the sample.

In FIG. 8A, the illumination mask includes an illumination pupil 44A having an oval-like shaped aperture which generates an illumination spot 15A on the surface of the sample. The illumination pupil 44B shown in FIG. 8B is configured to have substantially the same minor axis but larger eccentricity (i.e., stretched oval-like shape). This illumination pupil provides a smaller illumination spot 15B, at least along the horizontal axis, but still allows substantially the same or similar collection region 62.

In FIG. 8C, the illumination mask defines an illumination pupil in the form of three spaced apart transmission regions (apertures) 44C. The multi-region illumination pupil 44C is configured such that the shape and size of the diffraction lobes (being an image of the illumination pupil) match the blocking regions of the collection mask 25. As indicated above, the use of a larger effective area of the illumination pupil allows for reducing the size of the illumination spot 15C thus providing higher resolution of defect detection along the inspected sample. It should be noted, that the relationship between the area of the illumination pupil and the size/area of the illuminating spot on the surface of the sample are interconnected being typically a Fourier pair, and thus determine also the shape of the illuminating spot.

Figure 9:
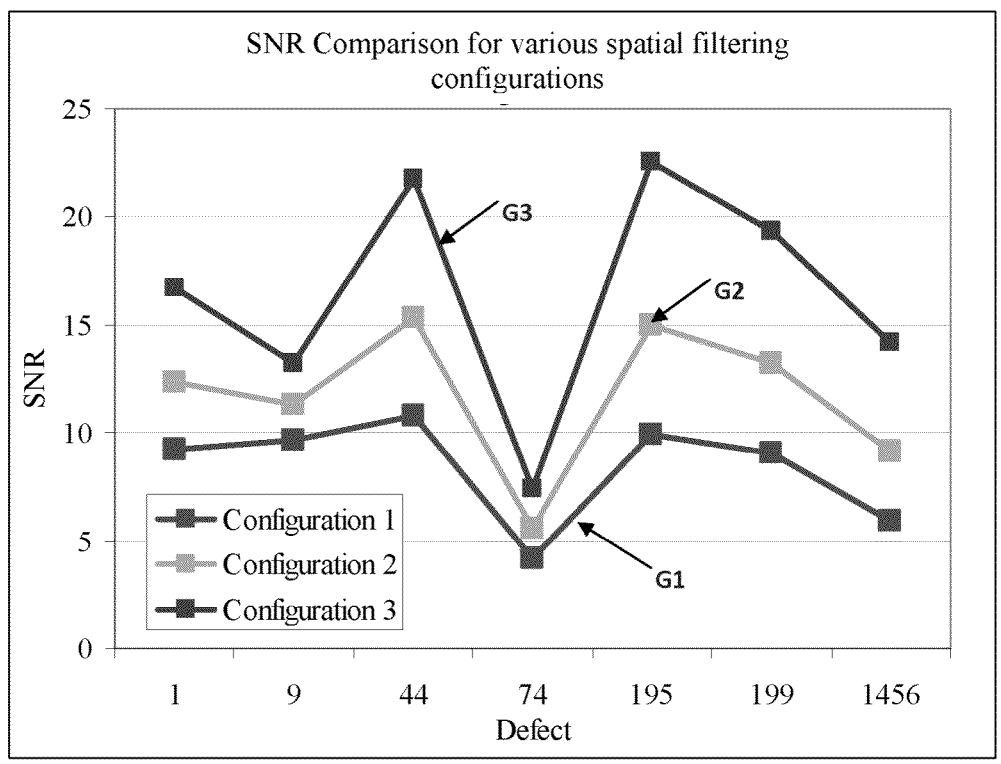
FIG. 9 shows the SNR of measurements as a function of defect type for three illumination masks as shown in FIGS. 8A to 8C.

FIG. 9 shows signal to noise ratio (SNR) measurements performed using three illumination masks as shown in FIGS. 8A to 8C. In this figure, graphs G1, G2 and G3 correspond to the use of illumination masks 44A, 44B and 44C respectively. It can be seen that for each and every numbered defect on a test sample, a higher value of SNR is achieved with the illumination mask 44C providing larger illumination pupil and smaller illumination spot.

Figure 10A:
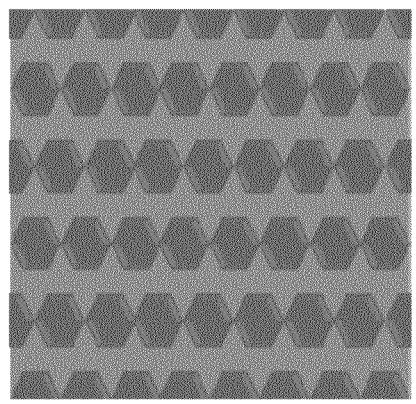
FIGS. 10A to 10D illustrate a hexagonal periodic pattern (FIG. 10A), diffraction response from the pattern (FIG. 10B) and diffraction response utilizing the technique of the present invention (FIGS. 10C and 10D)
Figure 10B:
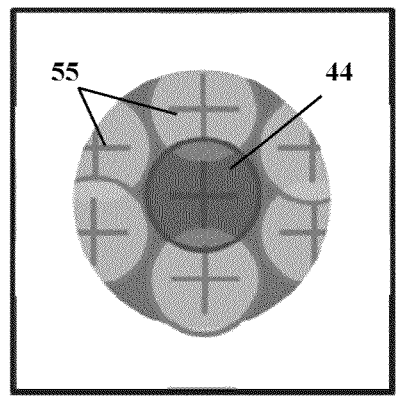
Figure 10C:
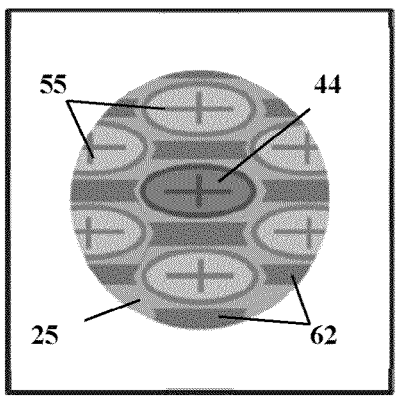
Figure 10D:
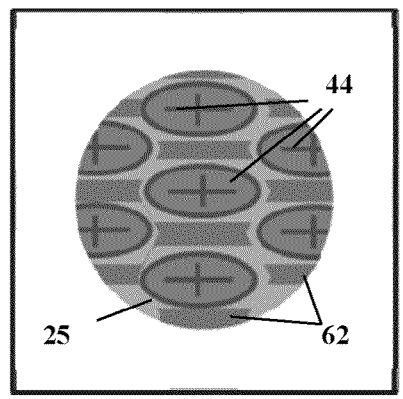

Reference is made to FIGS. 10A to 10D illustrating one other example of a patterned sample and its response. FIG. 10A shows an illustration of a hexagonal periodic pattern on a surface of a wafer/sample; FIG. 10B illustrates diffraction response including diffraction lobes 55 and showing an illumination pupil 44 associated with the pattern of FIG. 10A; FIG. 10C illustrates diffraction response associated with one embodiment of the invention; FIG. 10D illustrates diffraction response associated with one other embodiment of the present invention.

The conventional DF imaging techniques cannot be used in such a patterned sample due to the visible overlap of diffraction lobes 55, as can be seen in FIG. 10B. The diffraction lobes 55 overlap leaves no room for collection of scattered light for implementing of DF imaging techniques. Each of the diffraction lobes 55 is a copy of the illumination pupil 44 (in conjugated planes) and the pattern created by the centers of the lobes is uniquely defined by the geometry of the pattern (being an inverse lattice, i.e., the Fourier transform of pattern). By reducing the size of the illumination aperture 44, the diffraction lobes become separated and collection of scattered light is possible. However, the technique of the present invention provides a more clever way for separating the diffraction lobes.

FIG. 10C illustrates diffraction lobes pattern created when inspecting the hexagonal patterned sample using a system according to an embodiment of the present invention. According to this embodiment, the illumination pupil 44 is configured to have an oval-like shape, reducing the size of the illumination pupil along one axis while maintaining its size along other axis (horizontal and vertical axes as seen in FIG. 10C). The diffraction lobes 55, being images of the illumination pupil 44, become smaller along the appropriate axis and thus reducing their overlap. This enables a use of a collection mask 25 which is configured in accordance to the pattern of the diffraction lobes to block light components associated with the diffracted lobes whilst transmitting at least some light components associated with scattered light from the sample. The collection mask is 25 configured to block the diffraction lobes 55 and leave open transmitting regions 62 (areas) for collecting of signal of scattered light components originating from defects in the pattern. Reducing the size of the illumination pupil however results in increase of the size of the illumination spot on the surface of the sample, creating a tradeoff between collection of scattered light and accuracy of localizing a potential defect.

One other embodiment of the technique of the present invention is exemplified in FIG. 10D illustrating a use of illumination mask including array of apertures 44. In FIG. 10D the collection mask 25 is configured in accordance with the geometry of the lobe centers, given by the wafer pattern, however using an illumination pupil in the form of array of apertures 44 being configured as the negative of the collection mask 25, the effective spot size is reduced. It should be noted the diffraction lobes resulting from such illumination of the patterned sample overlap with the location of the illumination apertures and therefore are not visible in the figure. Utilizing such an illumination mask enables creating a desirably small illumination spot on the surface of the sample while maintaining relatively large separation between diffraction lobes for collection of scattered light.

Figure 11A:
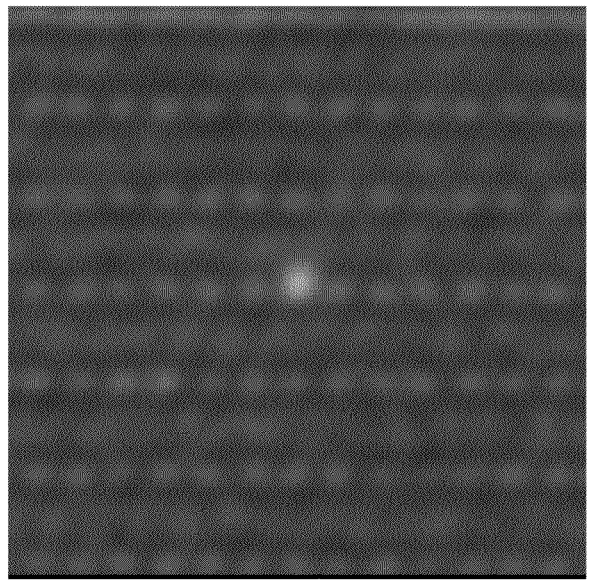
FIGS. 11A to 11B show experimental results of defects inspection in a patterned sample using typical scattered light (dark-field) inspection and the technique of the present invention respectively.
Figure 11B:
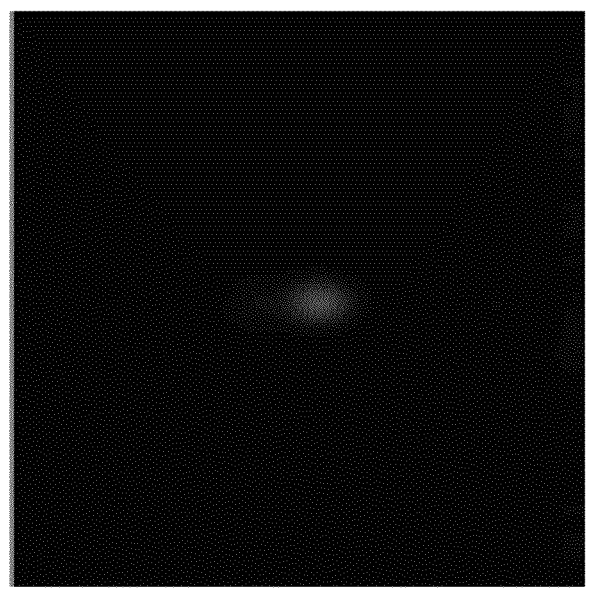

The improved SNR is further exemplified in FIGS. 11A and 11B showing experimental results for detection of a defect in a patterned sample. FIG. 11A shows scattered light inspection results, i.e., dark-field mode based on collection of the scattered light for detection of a defect, without blockage of diffraction lobes returned from the pattern. As indicated above, the scattered light inspection technique is used when the features of the pattern are of a dimension smaller than the optical resolution of the inspection system. The small features of the pattern are not fully resolved in the image, but light scattered from defects enables the defect detection. The results shown in FIG. 11A provide SNR of 15.8.

FIG. 11B shows the results of inspection using the system of the present invention and utilizing an illumination mask having an illumination pupil similar to illumination pupil 44A shown in FIG. 8A. By blocking the diffraction lobes returned from the pattern, and by appropriate tailoring of the illumination pupil to provide sufficient light intensity while maintaining a desirably small illumination spot of the surface of the sample, the inspection could provide SNR of 48.1. Such signal to noise ratio enables accurate detection of defects and reduces a number of false detection or missed defects.

In this connection, reference is made to FIG. 12 and FIGS. 13A-13B. FIG. 12 compares the efficiency of defect detection using different inspection techniques and utilizing different geometrical resolutions of inspection on samples having a pattern illustrated in FIG. 6A. Generally, three main types of defects may occur in such patterned samples: a missing pattern defect (shown in FIG. 13A), a bridge defect (shown in FIG. 13B), and foreign-particle associated defects (which is not specifically shown), i.e. defects associated with external particles such as dust particles located on the patterned sample.

FIG. 12 shows the inspection results obtained using scattered light (T1) in the typical DF mode, BF at geometrical resolution having pixel size of 100 nm (T2) and pixel size of 70 nm (T3), and the technique of the present invention with geometrical resolution having pixel size of 140 nm (T4) and of 190 nm (T5). As seen from the figure, the use of typical DF (scattered light) and bright-field inspection techniques provide only very limited detection of pattern-related defects. This is because the features of the pattern are smaller than the optical resolution of the inspection system and therefore cannot be fully resolved. As for the technique of the present invention, although it provides similar detection rate of foreign particles on the sample, as the typical DF and BF modes, the technique of the present invention provides an increased detection rate for pattern-related defects, such as missing pattern and bridges through features of the pattern. Detection of such pattern-related defects is important for increasing the yield of production of patterned samples.

It should be noted that the technique of the present invention is aimed at optimizing light collection in dark field imaging systems by both optimizing the collection region and optimizing the effective size of the illumination pupil(s) within the system. It should be understood that the illumination channel and the collection channel are interchangeable between them and thus are the illumination and collection masks. The larger the total transmitting area of each of the illumination and collection masks, the higher the SNR achieved. This area can be enlarged in the illumination channel, the collection channel or preferably in both channels. Such configuration can be implemented in non-coherent (or partially coherent) DF imaging, for example as based on the conventional optical microscopes. In such non coherent DF imaging systems a light source is used for illumination the sample, while light is collected via an optical system utilizing a collection mask. As indicated above, the illumination and collection masks are interchangeable between them to thereby enable non-coherent DF imaging according to the technique of the present invention.

As indicated above, dark field imaging may utilize scattered light collection at different orientations relative to the illumination path. The scattered light may be collected outside the propagation of zero order of diffraction, around the angular orientation of the specular reflection. The use of collection mask is preferred for any collection angle, for blocking the diffraction lobes and thus increasing the SNR of defect detection. The design of appropriate illumination mask according to the invention is aimed at optimizing the effective collection area/region while effectively blocking light components diffracted from the periodic pattern on the sample.

According to the above, the present invention utilizes a collection mask including an array of blocking regions for blocking light components associated with diffraction response of the pattern, and an illumination pupil of any suitable shape, e.g., circular or oval-like provided the illumination aperture(s) is/are in proper alignment/relation with the blocking regions of the collection mask. The technique of the present invention provides for optimizing a relation between the illumination spot size and effective collection area/region, thus providing high efficiency dark field inspection (higher SNR and resolution). Further, the collection and illumination masks of the invention may be removable and replaceable to enable inspection of a variety of patterned samples. The system for inspection of patterned sample according to the invention is capable of operating in dark-field inspection mode, and also, by removal of at least the collection mask, provides operation in bright field inspection mode.

Those skilled in the art will readily appreciate that various modifications and changes can be applied to the embodiments of the invention as hereinbefore described without departing from its scope defined in and by the appended claims.

What is claimed is:

1. A method for use in optical inspection of patterned samples, the method comprising:
   selecting illumination and collection masks for locating in illumination and collection channels respectively, in conjugate planes, being spectral planes with respect to an inspection plane defined by a sample under inspection, wherein said selecting comprises:
   selecting first and second spatial patterns of features for the illumination and collection masks, in accordance with a known diffraction response from the sample under inspection to illumination by a given illumination spot, such that the first and second spatial patterns are formed by light transmitting and blocking regions, defining, respectively, a dimension of an illuminating spot and a numerical aperture of the illumination channel, and a dimension of a light collection region;
   providing a predetermined angular orientation of the illumination channel with respect to the inspection plane, and a predetermined angular orientation of the collection channel with respect to the inspection plane, thereby providing that light components of first structured light created by light passage through the illumination mask are in a predetermined alignment with spaces between light components of second structured light created by light passage through the collection mask, determining a desired relation between the collection region defined by the light components of the second structured light and the dimension of the illumination spot;

illuminating a sample with light propagating through the illumination mask along the illumination channel having said numerical aperture and having said predetermined angular orientation with respect to an inspection plane, thereby creating the illuminating spot on the sample and causing the diffraction response from the sample;

collecting light returned from the sample through the collection mask along the collection channel of the predetermined angular orientation with respect to the inspection plane and allow propagation of the collected light to a detection plane.

2. The method of claim 1, wherein said predetermined alignment between the light components of the first structured light created by light passage through the first spatial pattern and the light components of the second structured light created by light passage through the second spatial pattern are selected to block specular reflection of light from the sample under inspection, and thereby prevent its propagation to the detection plane.

3. The method of claim 1, wherein said angular orientations of the illumination and collection channels with respect to the inspection plane define a normal incident mode, comprising transmitting light through a common imaging optics of the illumination and collection channels.

4. The method of claim 1, wherein said angular orientations of the illumination and collection channels with respect to the inspection plane are different according to oblique incidence inspection mode.

5. The method of claim 1, wherein the first spatial pattern of features formed by the light transmitting and blocking regions of the illumination mask is selected to define at least one oval-like transmitting region.

6. The method of claim 5, wherein the first spatial pattern of features formed by the light transmitting and blocking regions of the illumination mask is selected to define a one-dimensional or two-dimensional array of the oval-like transmitting regions.

7. The method of claim 6, wherein a distance between centers of adjacent transmitting regions in the illumination mask is selected as a predetermined function of a pitch of a pattern on the sample under inspection.

8. The method of claim 1, wherein said selecting comprises utilizing known data indicative of the diffraction response of the sample under inspection to illumination of given illumination parameters including at least a wavelength of illumination.

9. A method for use in optical inspection of patterned samples, the method comprising:

providing data indicative of a diffraction response of a sample under inspection to illumination of given illumination parameters including at least a wavelength of illumination, and providing data indicative of a spatial pattern of features of a collection mask to be used in a collection channel of an optical inspection system aimed at blocking diffraction lobes associated with said diffraction response;

utilizing said data indicative of the diffraction response of the sample under inspection and said data indicative of the collection mask "to select" a spatial pattern of features for an illumination mask, to be used in an illumination channel of the optical inspection system, said selecting comprising selection of geometry and arrangement of light transmitting regions in the illumination mask to provide a desired illumination spot size and a desired alignment between light components of first structured light created by light passage through the illumination mask and spaces between light components of second structured light created by light passage through the pattern of the collection mask to provide a desired relation between a collection region defined by the pattern of the collection mask and the dimension of the illumination spot defined by light passage through the pattern of the illumination mask; and accommodating the illumination and collection masks in conjugate spectral planes with respect to an inspection plane in respectively, the illumination and collection channels, and illuminating the sample with light propagating through the illumination mask along the illumination channel and collecting light returned from the sample through the collection mask along the collection channel and allow propagation of the collected light to a detection plane.

* * * * *